United States Patent [19]

Nelson et al.

[11] Patent Number: 5,770,029
[45] Date of Patent: Jun. 23, 1998

[54] INTEGRATED ELECTROPHORETIC MICRODEVICES

[75] Inventors: Robert J. Nelson, Alameda; Herbert H. Hooper, Belmont, both of Calif.; James Landers, Rochester, Minn.

[73] Assignee: Soane Biosciences, Hayward, Calif.

[21] Appl. No.: 690,307

[22] Filed: Jul. 30, 1996

[51] Int. Cl.$^6$ .......................... G01N 27/26; G01N 27/447
[52] U.S. Cl. ............................................. 204/604; 204/453
[58] Field of Search ..................................... 204/453, 604

[56] References Cited

U.S. PATENT DOCUMENTS

| 4,908,112 | 3/1990 | Pace ..................................... 210/198.2 |
| 5,126,022 | 6/1992 | Soane et al. ............................ 204/458 |
| 5,132,012 | 7/1992 | Miura et al. ........................... 210/198.2 |
| 5,296,114 | 3/1994 | Manz ...................................... 204/451 |
| 5,318,680 | 6/1994 | Fishman et al. ........................ 204/453 |
| 5,423,966 | 6/1995 | Wiktorowicz ............................ 204/453 |

FOREIGN PATENT DOCUMENTS

| 5164737 | 6/1993 | Japan ................................... 204/43.3 |
| WO93/05390 | 3/1993 | WIPO . |

OTHER PUBLICATIONS

Harrison et al, "Micromachining a Miniaturized Capillary Electrophoresis–Based Chemical Analysis System on a Chip," Science No month available (1992) 261: 895.

Jacobsen et al., "Precolumn Reactions with Electrophoretic Analysis Integrated on a Microchip," Anal. Chem. (1994) 66:4127–4132.

Effenhauser et al., "High–Speed Separation of Antisense Oligonucleotides on a Micromachined Capillary Electrophoresis Device," Anal. Chem. No month available (1994) 66:2949.

Tomlinson et al., "Enhancement of Concentration Limits of Detection in CE and CE–MS: A Review of On–Line Sample Extraction, Cleanup, Analyte Preconcentration, and Microreactor Technology," J. Cap. Elec. No month available (1995) 2: 247–266.

Beckers & Ackermans, The Effect of Sample Stacking for High Performance Capillary Electrophoresis J. Chromatogr. No month available (1993) 629: 371–378.

Chien & Burgi, "Field Amplified Sample Injection in High–Performance Capillary Electrophoresis," J. Chromatogr. No month avalialbe (1991) 559: 141–152.

Stegehuis et al., "Isotachophoresis as an On–Line Concentration Pretreatment Technique in Capillary Electrophoresis," J. Chromatogr. No month available (1991) 538: 393–402.

Kasicka & Prusik, "Isotachophoretic Electrodesorption of Proteins from an Affinity Adsorbent on a Microscale," J. Chromatogr. No month available (1983) 273:117128.

Cai & El Rassi, "On–Line Preconcentration of Triazine Herbicides with Tandem Octadecyl Capillaries–Capillary Zone Electrophoresis," J. Liq. Chromatogr. No month available (1992) 15:1179–1192.

(List continued on next page.)

*Primary Examiner*—Kathryn L. Gorgos
*Assistant Examiner*—John S. Starsiak, Jr.
*Attorney, Agent, or Firm*—Flehr Hohbach Test Albritton & Herbert LLP

[57] ABSTRACT

Integrated electrophoretic microdevices comprising at least an enrichment channel and a main electrophoretic flowpath are provided. In the subject integrated devices, the enrichment channel and the main electrophoretic flowpath are positioned so that waste fluid flows away from said main electrophoretic flowpath through a discharge outlet. The subject devices find use in a variety of electrophoretic applications, including clinical assays.

14 Claims, 5 Drawing Sheets

OTHER PUBLICATIONS

Cai & El Rassi, "Selective On–Line Preconcentration of Proteins by Tandem Metal Chelate Capillaries–Capillary Zone Electrophoresis," J. Liq. Chromatogr. No month available (1993) 16:2007–2024.

Cole & Kennedy, "Selective Preconcentration for Capillary Zone Electrophoresis Using Protein G Immunoaffinity Capillary Chromatography," Electrophoresis No month available (1995) 16:549–556.

Guzman, "Biomedical Applications of On–Line Preconcentration—Capillary Electrophoresis Using an Analyte Concentrator: Investigation of Design Options," J. Liq. Chromatogr. No month available (1995) 18:3751–3568.

INTEGRATED ELECTROPHORETIC MICRODEVICES

FIELD OF THE INVENTION

The field of the invention is electrophoresis.

BACKGROUND

Electrophoresis has become an indispensable tool of the biotechnology and other industries, as it is used extensively in a variety of applications, including the separation, identification and preparation of pure samples of nucleic acids, proteins, carbohydrates, the identification of a particular analyte in a complex mixture, and the like. Of increasing interest in the broader field of electrophoresis is capillary electrophoresis (CE), where particular entities or species are moved through a medium in an electrophoretic chamber of capillary dimensions under the influence of an applied electric field. Benefits of CE include rapid run times, high separation efficiency, small sample volumes, etc. Although CE was originally carried out in capillary tubes, of increasing interest is the practice of using microchannels or trenches of capillary dimension on a planar substrate, known as microchannel electrophoresis (MCE). CE and MCE are increasingly finding use in a number of different applications in both basic research and industrial processes, including analytical, biomedical, pharmaceutical, environmental, molecular, biological, food and clinical applications.

Despite the many advantages of CE and MCE, the potential benefits of these techniques have not yet been fully realized for a variety of reasons. Because of the nature of the electrophoretic chambers employed in CE and MCE, good results are not generally obtainable with samples having analyte concentrations of less than about $10^{-6}$ M. This lower analyte concentration detection limit has significantly limited the potential applications for CE and MCE. For example, CE and MCE have not found widespread use in clinical applications, where often an analyte of interest is often present in femto- to nanomolar concentration in a complex sample, such as blood or urine.

In order to improve the detection limits of CE, different techniques have been developed, including improved sample injection procedures, such as analyte stacking (Beckers & Ackermans, "The Effect of Sample Stacking for High Performance Capillary Electrophoresis" J. Chromatogr. (1993) 629:371–378), field amplification (Chien & Burgi, "Field Amplified Sample Injection in High-Performance Capillary Electrophoresis," J. Chromatogr. (1991) 559:141–152), and transient isotachophoresis (Stegehuis et al., "Isotachophoresis as an On-Line Concentration Pretreatment Technique in Capillary Electrophoresis," J. Chromatogr. (1991) 538:393–402), as well as improved sample detection procedures and "off-line" sample preparation procedures.

Another technique that has been developed to improve the detection limit achievable with CE has been to employ an analyte preconcentration device that is positioned directly upstream from the capillary, i.e. in an "on-line" or "single flow path" relationship. As used herein, the term "on-line" and "single flow path" are used to refer to the relationship where all of the fluid introduced into the analyte preconcentration component, i.e. the enriched fraction and the remaining waste fraction of the original sample volume, necessarily flows through the main electrophoretic portion of the device, i.e. the capillary tube comprising the separation medium. A review of the various configurations that have been employed is provided in Tomlinson et al, "Enhancement of Concentration Limits of Detection in CE and CE-MS: A Review of On-Line Sample Extraction, Cleanup, Analyte Preconcentration, and Microreactor Technology," J. Cap. Elec. (1995) 2:247–266, and the figures provided therein.

Although this latter approach can provide improved results with regard to analyte detection limits, particularly with respect to the concentration limit of detection, it can have a deleterious impact on other aspects of CE, and thereby reduce the overall achievable performance. For example, analyte peak widths can be broader in on-line or single flow path devices comprising analyte preconcentrators. there is continued interest in the development of improved CE devices capable of providing good results with samples having low concentrations of analyte, particularly analyte concentrations in the femtomolar to nanomolar range.

RELEVANT LITERATURE

MCE devices are disclosed in U.S. Pat. Nos. 5,126,022; 5,296,114; 5,180,480; 5,132,012; and 4,908,112. Other references describing MCE devices include Harrison et al., "Micromachining a Minitiarized Capillary Electrophoresis-Based Chemical Analysis System on a Chip," Science (1992) 261:895; Jacobsen et al., "Precolumn Reactions with Electrophoretic Analysis Integrated on a Microchip," Anal. Chem. (1994) 66:2949; Effenhauser et al., "High-Speed Separation of Antisense Oligonucleotides on a Micromachined Capillary Electrophoresis Device," Anal. Chem. (1994) 66:2949; and Woolley & Mathies, "Ultra-High-Speed DNA Fragment Separations Using Capillary Array Electrophoresis Chips," P.N.A.S. USA (1994) 91:11348.

Patents disclosing devices and methods for the preconcentration of analyte in a sample "on-line" prior to CE include U.S. Pat. Nos. 5,202,010; 5,246,577 and 5,340,452. A review of various methods of analyte preconcentration employed in CE is provided in Tomlinson et al., "Enhancement of Concentration Limits of Detection in CE and CE-MS: A Review of On-Line Sample Extraction, Cleanup, Analyte Preconcentration, and Microreactor Technology," J. Cap. Elec. (1995) 2:247–266.

SUMMARY OF THE INVENTION

Integrated electrophoretic microdevices comprising at least an enrichment channel and a main electrophoretic flow path, as well as methods for their use in electrophoretic applications, are provided. The enrichment channel serves to enrich a particular fraction of a liquid sample for subsequent movement through the main electrophoretic flowpath. In the subject devices, the enrichment channel and electrophoretic flowpath are positioned such that waste fluid from the enrichment channel does not flow through the main electrophoretic flowpath, but instead flows through a discharge outlet. The subject devices find use in a variety of electrophoretic applications where entities are moved through a medium in response to an applied electric field.

DESCRIPTION OF THE SPECIFIC EMBODIMENTS

Integrated electrophoretic microdevices comprising at least an enrichment channel and a main electrophoretic flowpath are provided. The enrichment channel serves to enrich a particular analyte comprising fraction of a liquid sample. The enrichment channel and main electrophoretic flowpath are positioned in the device so that waste fluid from the enrichment channel does not flow through the main electrophoretic channel, but instead flows away from the main electrophoretic flowpath through a discharge outlet. The subject devices may be used in a variety of electrophoretic applications, including clinical assay applications. In further describing the invention, the devices will first be described in general terms followed by a discussion of representative specific embodiments of the subject devices with reference to the figures.

The subject device is an integrated electrophoretic microdevice. By integrated is meant that all of the components of the device, e.g. the enrichment channel, the main electrophoretic flowpath, etc., are present in a single, compact, readily handled unit, such as a chip, disk or the like. As the devices are electrophoretic, they are useful in a wide variety of the applications in which entities, such as molecules, particles, cells and the like are moved through a medium under the influence of an applied electric field. Depending on the nature of the entities, e.g. whether or not they carry an electrical charge, as well as the surface chemistry of the electrophoretic chamber in which the electrophoresis is carried out, the entities may be moved through the medium under the direct influence of the applied electric field or as a result of bulk fluid flow through the pathway resulting from the application of the electric field, e.g. electroosmotic flow (EOF). The microdevices will comprise a microchannel as the main electrophoretic flowpath. By microchannel is meant that the electrophoretic chamber of the main electrophoretic flowpath in which the medium is present is a conduit, e.g. trench or channel, having a cross sectional area which provides for capillary flow through the chamber, where the chamber is present on a planar substrate, as will be described below in greater detail.

Critical to the subject device is an enrichment channel that comprises a sample inlet, a waste fluid outlet, an internal enrichment medium for enriching a particular fraction of a sample, and, optionally, an enriched fraction fluid outlet. The purpose of the enrichment channel is to process the initial sample to enrich for a particular fraction thereof, where the particular fraction being enriched comprises the analyte or analytes of interest. The enrichment channel thus serves to selectively retain and separate the target analyte comprising fraction from the remaining components or the waste portion of the initial sample volume. Depending on the particular application in which the device is employed, the enrichment channel can provide for a number of different functions. The enrichment channel can serve to place the analyte of interest into a smaller volume than the initial sample volume, i.e. it can serve as an analyte concentrator. Furthermore, it can serve to prevent potentially interfering sample components from entering and flowing through the main electrophoretic flowpath, i.e. it can serve as a sample "clean-up" means. In addition, the enrichment channel may serve as a microreactor for preparative processes on target analyte present in a fluid sample, such as chemical and enzymatic processes, e.g. labeling, protein digestion, and the like.

The enrichment channel may be present in the device in a variety of configurations, depending on the particular enrichment medium housed therein. The internal volume of the channel will usually range from about 1 pl to 1 µl, usually from about 1 pl to 100 nl, where the length of the channel will generally range from about 1 µm to 1 mm, usually 10 µm to 1 mm, and the cross-sectional dimensions (e.g. width, height) will range from about 1 µm to 100 µm, usually from about 10 µm to 40 µm. The cross-sectional shape of the channel may be circular, ellipsoid, square, or other convenient configuration.

A variety of different enrichment mediums may be present in the enrichment channel. Representative enrichment medium or means include those means described in the analyte preconcentration devices disclosed in U.S. Pat. Nos. 5,202,010; 5,246,577 and 5,340,452, as well as Tomlinson et al., supra, the disclosures of which are herein incorporated by reference. Specific enrichment means known in the art which may be adaptable for use in the subject integrated microchannel electrophoretic devices include: those employed in protein preconcentration devices described in Kasicka & Prusik, "Isotachophoretic Electrodesorption of Proteins from an Affinity Adsorbent on a Microscale," J. Chromatogr. (1983) 273:117128; capillary bundles comprising an affinity adsorbent as described in U.S. Pat. No. 5,202,101 and WO 93/05390; octadodecylsilane coated solid phases as described in Cai & El Rassi, "On-Line Preconcentration of Triazine Herbicides with Tandem Octadecyl Capillaries-Capillary Zone Electrophoresis," J. Liq. Chromatogr. (1992) 15:1179–1192; solid phases coated with a metal chelating layer as described in Cai & El Rassi, "Selective On-Line Preconcentration of Proteins by Tandem Metal Chelate Capillaries-Capillary Zone Electrophoresis," J. Liq. Chromatogr. (1993) 16:2007–2024; reversed-phase HPLC solid packing materials as described in U.S. Pat. No. 5,246,577, Protein G coated solid phases as described in Cole & Kennedy, "Selective Preconcentration for Capillary Zone Electrophoresis Using Protein G Immunoaffinity Capillary Chromatography," Electrophoresis (1995) 16:549–556; meltable agarose gels as described in U.S. Pat. No. 5,423,966; affinity adsorbent materials as described in Guzman, "Biomedical Applications of On-Line Preconcentration - Capillary Electrophoresis Using an Analyte Concentrator: Investigation of Design Options," J. Liq. Chromatogr. (1995) 18:3751–3568); and solid phase reactor materials as described in U.S. Pat. No. 5,318,680; the disclosures of which are herein incorporated by reference.

One class of enrichment media or materials that may find use as enrichment media are chromatographic media or materials, particularly absorptive phase materials. Such materials include: reverse phase materials, e.g. C8 or C18 compound coated particles; ion-exchange materials; affinity chromatographic materials in which a binding member is covalently bound to an insoluble matrix, where the binding member may be group specific, e.g a lectin, enzyme cofactor, Protein A and the like, or substance specific, e.g. antibody or binding fragment thereof, antigen for a particular antibody of interest, oligonucleotide and the like, where the insoluble matrix to which the binding member is bound may be particles, such as porous glass or polymeric beads, networks of glass strands or filaments, a plurality of narrow rods or capillaries, the wall of the channel and the like. Depending on the nature of the chromatographic material employed as the enrichment means, it may be necessary to employ a retention means to keep the chromatographic material in the enrichment channel. Conveniently, glass frits may be employed to cover the fluid outlets or inlets of the chamber, where the glass frits allow for fluid flow but not for particle or other insoluble matrix flow out of the enrichment channel. In embodiments where the enrichment means is a chromatographic material, typically sample will be introduced into, and allowed to flow through, the enrichment channel. As the sample flows through the enrichment channel, the analyte comprising fraction will be retained in the enrichment channel by the chromatographic material and the remaining waste portion of the sample will flow out of the channel through the waste outlet. Depending on the configuration of the device, the sample can be caused to flow through the enrichment channel a number of different ways. In some device configurations, it may be sufficient to allow the sample to flow through the means as a result of gravity forces on the sample. In other embodiments, active pumping means may be employed to move sample through the enrichment channel and enrichment means housed therein. In yet other embodiments of the subject invention, electrodes may be employed to apply an electric field which causes fluid to move through the enrichment channel. An elution liquid will then be caused to flow through the chromatographic material to release the enriched sample fraction from the material and carry it to the main electrophoretic flowpath. Generally, an applied electric field will be employed to move the elution liquid through the enrichment channel.

Instead of employing solid phase materials such as coated particles or other insoluble matrices as the enrichment means, one may employ a coated/impregnated membrane which provides for selective retention of the analyte comprising fraction of the sample while allowing the remainder of the sample to flow through the membrane and out of the enrichment means through the waste outlet. A variety of hydrophilic, hydrophobic and ion-exchange membranes have been developed for use in solid phase extraction which may find use in the subject invention. See Tomlinson et al., "Novel Modifications and Clinical Applications of Preconcentration-Capillary Electrophoresis-Mass Spectrometry," J. Cap. Elect. (1995) 2:97–104; and Tomlinson et al., "Improved On-line Membrane Preconcentration-Capillary Electrophoresis (mPC-CE),"J. High Res. Chromatogr. (1995) 18:381–3.

Electrophoretic gel media may also be employed as enrichment means in the subject applications. Gel media providing for a diversity of different sieving capabilities are known. By varying the pore size of the media, employing two or more gel media of different porosity, and/or providing for a pore size gradient and selecting the appropriate relationship between the enrichment channel and the main electrophoretic flowpath, one can ensure that only the analyte comprising fraction of interest of the initial sample enters the main electrophoretic flowpath. For example, one could have a device comprising an enrichment channel that intersects the main electrophoretic channel, where the enrichment channel comprises, in the direction of sample flow, a stacking gel of large porosity and a second gel of fine porosity, where the boundary between the gels occurs in the intersection of the enrichment channel and the main electrophoretic flowpath. In this embodiment, after sample is introduced into the stacking gel and an electric field applied to the gels in the enrichment channel, the sample components move through the stacking gel and condense into a narrow band at the gel interface in the intersection of the enrichment channel and main electrophoretic flowpath. A second electric field can then be applied to the main electrophoretic flowpath so that the narrow band of the enriched sample fraction moves into and through the main electrophoretic flowpath. Alternatively, the enrichment channel could comprise a gel of gradient porosity. In this embodiment, when the band(s) of interest reaches the intersection of the enrichment channel and electrophoretic flowpath, the band(s) of interest can then be moved into and along the main electrophoretic flowpath.

As mentioned above, the enrichment channel will comprise at least a sample inlet and waste outlet. Depending on the particular enrichment means housed in the enrichment channel, as well as the particular device configuration, the enrichment channel may have an additional fluid inlet, e.g. elution buffer inlet and/or outlet, e.g. enriched fraction fluid outlet. Where the enrichment channel is in direct fluid communication with the main electrophoretic channel, i.e. the enrichment channel and main electrophoretic flowpath are in juxtaposition and joined so that fluid flows from the enrichment channel immediately into the main electrophoretic flowpath, the enrichment channel will comprise, in addition to the waste outlet, a second or enriched fraction fluid outlet through which the enriched fraction of the sample flows into the main electrophoretic flowpath. When convenient, e.g. for the introduction of elution solvent into the enrichment channel, one may provide for a second fluid inlet into the enrichment channel from a fluid reservoir. To control bulk fluid flow through the enrichment channel, e.g. to prevent waste sample from flowing into the main electrophoretic flowpath, fluid control means, e.g. valves, membranes, etc., may be associated with each of the inlets and outlets. Where desirable for moving fluid and entities through the enrichment channel, e.g. sample, elution buffer, reagents, reactants, wash or rinse solutions, etc., electrodes may be provided capable of applying an electric field to the material and fluid present in the enrichment channel.

The next component of the subject devices is the main electrophoretic flowpath. The main electrophoretic flow path may have a variety of configurations, including tube-like, trench-like or other convenient configuration, where the cross-sectional shape of the flowpath may be circular, ellipsoid, square, rectangular, triangular and the like so that it forms a microchannel on the surface of the planar substrate in which it is present. The microchannel will have cross-sectional area which provides for capillary fluid flow through the microchannel, where at least one of the cross-sectional dimensions, e.g. width, height, diameter, will be at least about 1 $\mu$m, usually at least about 10 $\mu$m, but will not exceed about 200 $\mu$m, and will usually not exceed about 100 $\mu$m. Depending on the particular nature of the integrated device, the main electrophoretic flowpath may be straight, curved or another convenient configuration on the surface of the planar substrate.

The main electrophoretic flowpath, as well as any additional electrophoretic flowpaths, will have associated with it at least one pair of electrodes for applying an electric field to the medium present in the flow path. Where a single pair of electrodes is employed, typically one member of the pair will be present at each end of the pathway. Where convenient, a plurality of electrodes may be associated with the electrophoretic flowpath, as described in U.S. Pat. No. 5,126,022, the disclosure of which is herein incorporated by reference, where the plurality of electrodes can provide for precise movement of entities along the electrophoretic flowpath. The electrodes employed in the subject device may be any convenient type capable of applying an appropriate electric field to the medium present in the electrophoretic flowpath with which they are associated.

Critical to the subject invention is that the enrichment channel and the main electrophoretic flow path are positioned in the device so that substantially only the enriched fraction of the sample flows through the main electrophoretic flow path. To this end, the device will further comprise a discharge outlet for discharging a portion of sample other than the enriched fraction, e.g. the waste portion, away from the main electrophoretic flowpath. Thus, where the enrichment channel is in direct fluid communication with the main electrophoretic flowpath, the waste fluid flow path through the enrichment channel will be in an intersecting relationship with the main electrophoretic flowpath. In other embodiments of the subject invention where the enrichment channel and main electrophoretic flow path are connected by a second electrophoretic flowpath so that they are in indirect fluid communication, the waste flow path through the enrichment channel does not necessarily have to be in an intersecting relationship with the main electrophoretic flow path; the waste flow path and main electrophoretic flowpath could be parallel to one another.

The subject devices will also comprise a means for transferring the enriched fraction from the enrichment channel to the main electrophoretic flow path. Depending on the particular device configuration, the enriched fraction transfer means can be an enriched fraction fluid outlet, a secondary electrophoretic pathway, or other suitable transfer means. By having a second electrophoretic flowpath in addition to the main electrophoretic flowpath, the possibility exists to employ the second electrophoretic flowpath as a conduit for the enriched sample fraction from the enrichment channel to the main electrophoretic flowpath. In those embodiments where the waste outlet is the sole fluid outlet, the presence of a secondary electrophoretic flowpath will be essential, such that the enrichment channel and the main electrophoretic flowpath are in indirect fluid communication.

In addition to the main and any secondary electrophoretic flowpath serving as an enriched sample transfer means, the subject devices may further comprise one or more additional electrophoretic flowpaths, which may or may not be of capillary dimension and may serve a variety of purposes. With devices comprising a plurality of electrophoretic flowpaths, a variety of configurations are possible, such as a branched configuration in which a plurality of electrophoretic flowpaths are in fluid communication with the main electrophoretic flowpath. See U.S. Pat. No. 5,126,022, the disclosure of which is herein incorporated by reference.

The main electrophoretic flowpath and/or any secondary electrophoretic flow paths present in the device may optionally comprise, and usually will comprise, fluid reservoirs at one or both termini, i.e. either end, of the flowpaths. Where reservoirs are provided, they may serve a variety of purposes, such as a means for introducing buffer, elution solvent, reagent, rinse and wash solutions, and the like into the main electrophoretic flow path, receiving waste fluid from the electrophoretic flow path, and the like.

Another optional component that may be present in the subject devices is a waste fluid reservoir for receiving and storing the waste portion of the initial sample volume from the enrichment channel, where the waste reservoir will be in fluid communication with the discharge outlet. Depending on the particular device configuration, the discharge outlet may be the same as, or distinct from, the waste outlet, and may open into a waste reservoir or provide an outlet from the device. The waste reservoir may be present in the device as a channel, compartment, or other convenient configuration which does not interfere with the other components of the device.

The subject device may also optionally comprise an interface means for assisting in the introduction of sample into the sample preparation means. For example, where the sample is to be introduced by syringe into the device, the device may comprise a syringe interface which serves as a guide for the syringe needle into the device, as a seal, and the like.

Depending on the particular configuration and the nature of the materials from which the device is fabricated, at least in association with the main electrophoretic flowpath will be a detection region for detecting the presence of a particular species in the medium contained in the electrophoretic flowpath. At least one region of the main electrophoretic flowpath in the detection region will be fabricated from a material that is optically transparent, generally allowing light of wavelengths ranging from 180 to 1500 nm, usually 220 to 800 nm, more usually 250 to 800 nm, to have low transmission losses. Suitable materials include fused silica, plastics, quartz glass, and the like.

The integrated device may have any convenient configuration capable of comprising the enrichment channel and main electrophoretic flowpath, as well as any additional components. Because the devices are microchannel electrophoretic devices, the electrophoretic flowpaths will be present on the surface of a planar substrate, where the substrate will usually, though not necessarily, be covered with a planar cover plate to seal the microchannels present on the surface from the environment. Generally, the devices will be small, having a longest dimension in the surface plane of no more than about 200 mm, usually no more than about 100 mm so that the devices are readily handled and manipulated. As discussed above, the devices may have a variety of configurations, including parallelepiped, e.g. credit card or chip like, disk like, syringe like or any other compact, convenient configuration.

The subject devices may be fabricated from a wide variety of materials, including glass, fused silica, acrylics, thermoplastics, and the like. The various components of the integrated device may be fabricated from the same or different materials, depending on the particular use of the device, the economic concerns, solvent compatibility, optical clarity, color, mechanical strength, and the like. For example, both the planar substrate comprising the microchannel electrophoretic flowpaths and the cover plate may be fabricated from the same material, e.g. polymethylmethacrylate (PMMA), or different materials, e.g. a substrate of PMMA and a cover plate of glass. For applications where it is desired to have a disposable integrated device, due to ease of manufacture and cost of materials, the device will typically be fabricated from a plastic. For ease of detection and fabrication, the entire device may be fabricated from a plastic material that is optically transparent, as that term is defined above. Also of interest in certain applications are plastics having low surface charge under conditions of electrophoresis. Particular plastics finding use include polymethylmethacrylate, polycarbonate, polyethylene terepthalate, polystyrene or styrene copolymers, and the like.

The devices may be fabricated using any convenient means, including conventional molding and casting techniques. For example, with devices prepared from a plastic material, a silica mold master which is a negative for the channel structure in the planar substrate of the device can be prepared by etching or laser micromachining. In addition to having a raised ridge which will form the channel in the substrate, the silica mold may have a raised area which will provide for a cavity into the planar substrate for housing of the enrichment channel. Next, a polymer precursor formulation can be thermally cured or photopolymerized between the silica master and support planar plate, such as a glass plate. Where convenient, the procedures described in U.S. Pat. No. 5,110,514, the disclosure of which is herein incorporated by reference, may be employed. After the planar substrate has been fabricated, the enrichment channel may be placed into the cavity in the planar substrate and electrodes introduced where desired. Finally, a cover plate may be placed over, and sealed to, the surface of the substrate, thereby forming an integrated device. The cover plate may be sealed to the substrate using any convenient means, including ultrasonic welding, adhesives etc.

Generally, prior to using the subject device, a suitable first or electrophoretic medium will be introduced into the electrophoretic flowpaths or microchannels of the device, where the first medium will be different from the enrichment medium present in the enrichment channel. Electrophoretic media is used herein to refer to any medium to which an electric field is applied to move species through the medium. The electrophoretic media can be conveniently introduced through the reservoirs present at the termini of the electrophoretic flowpaths or directly into the channels or chambers of the electrophoretic flowpaths prior to sealing of the cover plate to the substrate. Any convenient electrophoretic medium may be employed. Electrophoretic mediums suitable for use, depending on the particular application, include buffers, crosslinked and uncrosslinked polymeric media, organic solvents, detergents, and the like, as disclosed in Barron & Blanch, "DNA Separations by Slab Gel and Capillary Electrophoresis: Theory and Practice," Separation and Purification Methods (1995) 24:1–118, as well as in U.S. application Ser. Nos. 08/241,048 now U.S. Pat. No. 5,569,364, 08/636,599 and 08/589,150, the disclosures of which are herein incorporated by reference. Of particular interest as electrophoretic media are cellulose derivatives, polyacrylamides, polyvinyl alcohols, polyethylene oxides, and the like.

Figure 1:
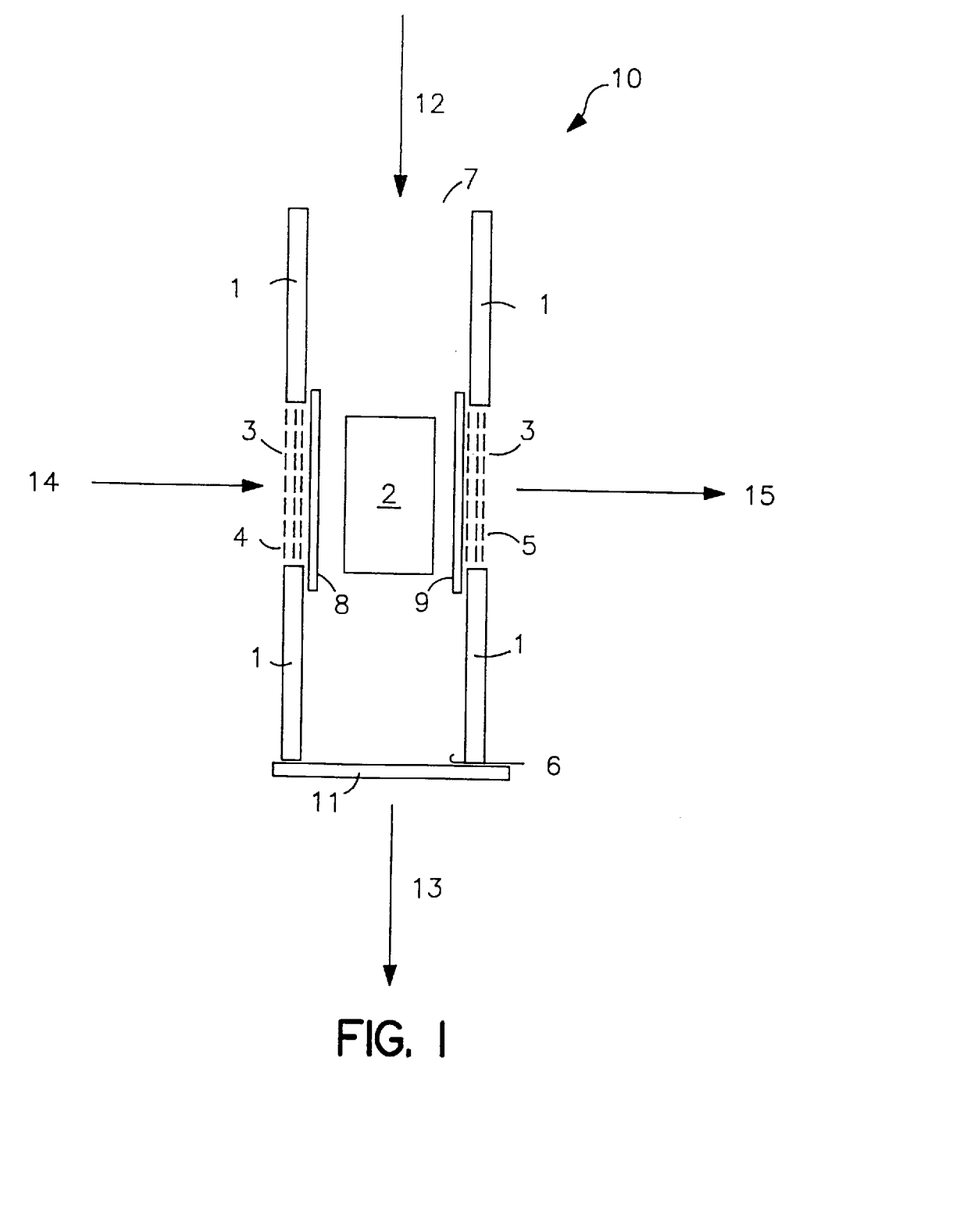
FIG. 1 provides a diagrammatic view of an enrichment channel for use in a device according to the subject invention.

The subject invention will now be further described in terms of the figures. FIG. 1 provides a diagrammatic view of an enrichment channel which may find use in the devices of the subject invention. Enrichment channel 10 comprises side walls 1 which enclose reverse phase C18 material 2. Channel 10 further comprise fluid inlets 7 and 4 and fluid outlets 5 and 6. For controlling fluid flow through the channel inlets and outlets, valves 8, 9 and 11 are provided. Glass frits 3 allow for fluid flow through inlet 4 and outlet 5 but restrain reverse phase material 2 in the channel. In using this enrichment channel, sample is introduced through sample inlet 7 in the direction of flow path 12. As sample moves through channel 10, the analyte comprising fraction is retained on reverse phase material 2 while the remaining waste fraction of the sample flows out waste outlet 6 along flow path 13. Valves 8 and 9 are closed to prevent sample from flowing or "bleeding" out inlet 4 or outlet 5. After the sample has flowed through channel 10, valve 11 is shut and valves 8 and 9 are opened. Elution buffer is then introduced into channel 10 through glass frit 3 and inlet 4 in the direction of flow path 14. As elution buffer moves through material 2, the retained fraction of the sample is released and carried with the elution buffer out enriched fraction outlet 5 through frit 3 along flow path 15.

Figure 2:
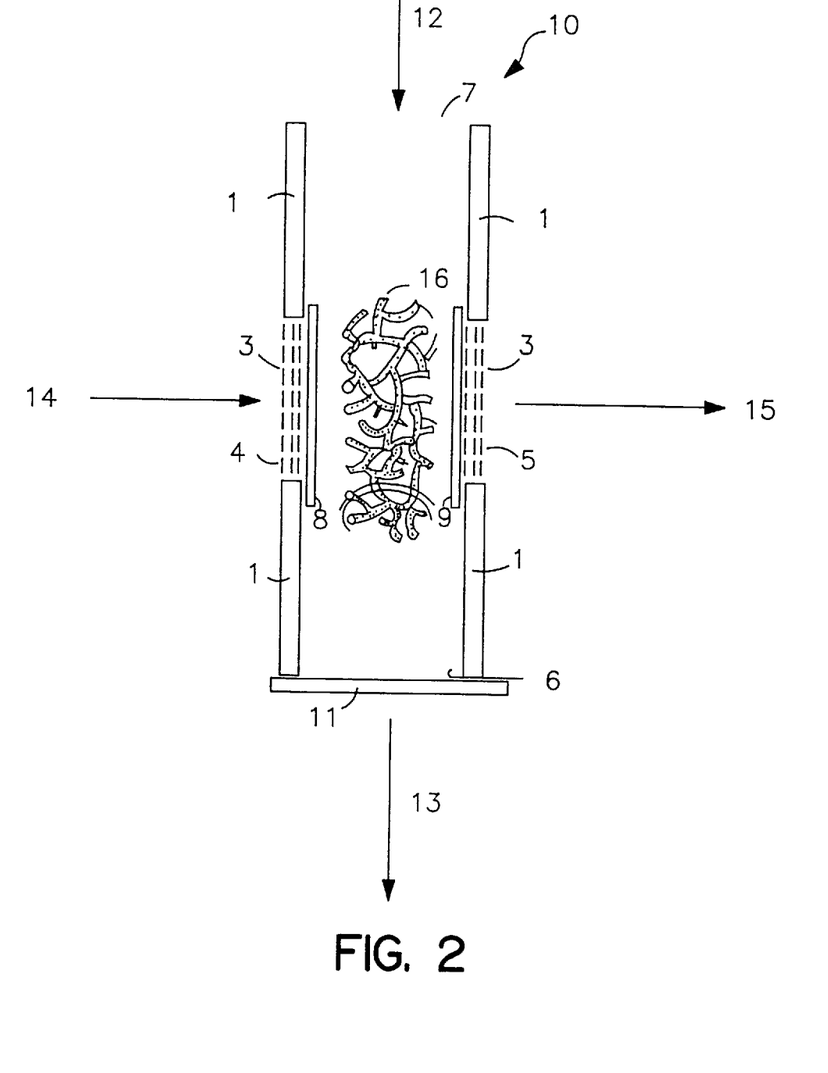
FIG. 2 provides a diagrammatic view of an alternative embodiment of an enrichment channel also suitable for use in the subject device.

In FIG. 2, the same enrichment channel as shown in FIG. 1 is depicted with the exception that reverse phase material 2 is replaced by a network of crosslinked glass filaments 16 to which binding pair member is covalently bound.

Figure 3A:
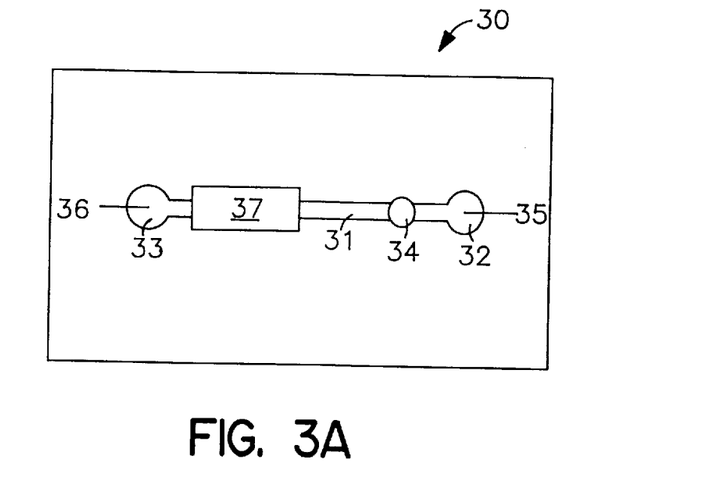
FIG. 3A provides a top diagrammatic view of a device according to the subject invention.

FIG. 3A provides a diagrammatic top view of a credit card shaped (parallelepiped) device according to the subject invention. Device 30 comprises main electrophoretic flow path 31 having reservoir 32 at a first end and reservoir 33 at a second end. In direct fluid communication with main electrophoretic flow path 31 is enrichment channel 34 (seen from overhead). Electrodes 35 and 36 are provided for applying an electric field to the medium present in electrophoretic flow path 31. Detection region 37 is positioned over electrophoretic flow path 31 for viewing analyte present in the medium comprised in the flow path. A detection region can also be provided over the enrichment channel 34. Although the device shown in FIG. 3A comprises a single enrichment channel, additional enrichment channels could be provided in the flow path, including in the detection region.

Figure 3B:
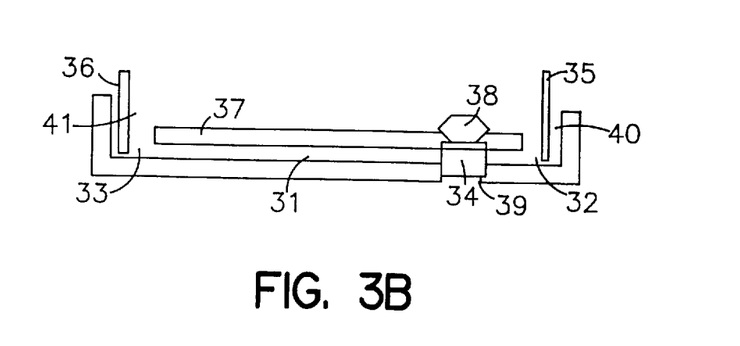
FIG. 3B provides a side view of the device of FIG. 3A.

FIG. 3B provides a diagrammatic side view of the device depicted in FIG. 3A. In using this embodiment of the subject invention, sample is introduced through syringe interface 38 into enrichment channel 34, where the analyte comprising fraction of the sample is retained as the waste fraction flows out of the enrichment channel 34 through discharge outlet 39 and out of the device. Elution buffer is then introduced into reservoir 32 through port 40. An electric field is then applied between electrodes 35 and 36 causing elution buffer to migrate from reservoir 32 through enrichment channel 34 and along electrophoretic flow path 31 to reservoir 33. As the elution buffer moves through enrichment channel 34, it releases the retained analyte comprising fraction of the initial sample volume and carries it into electrophoretic flow path 31.

Figure 4:
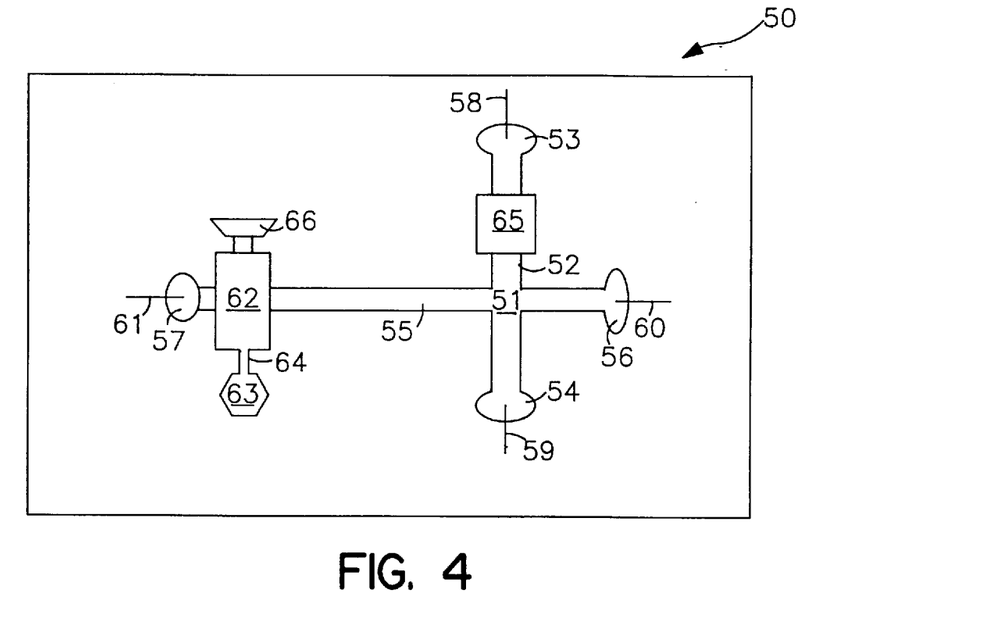
FIG. 4 provides a diagrammatic top view of another embodiment of the subject invention.

FIG. 4 shows a diagrammatic view of an embodiment of the subject invention in which the enrichment channel 62 is separated from main electrophoretic flow path 52 by secondary electrophoretic flow path 55. With device 50, sample is introduced into enrichment channel 62 through syringe interface 66. As sample flows through enrichment channel 62, waste sample flows through discharge outlet 64 into waste reservoir 63. An electric field is then applied between electrodes 61 and 60 causing elution buffer present in reservoir 57 to move through enrichment channel 62, resulting in the release of analyte. Analyte is then carried along secondary electrophoretic flowpath 55 along with the elution buffer. When analyte reaches intersection 51, the electric field between electrodes 60 and 61 is replaced by an electric field between electrodes 59 and 58. In this and other analogous embodiments of the subject invention, the time at which analyte reaches intersection 51 may be determined by detecting the presence of analyte in the intersection or by empirically determining the time at which the analyte should reach the intersection, based on the particular nature of the analyte, the medium in the flowpath, the strength of the electric field, and the like. Following application of the electric field between electrodes 59 and 58, which are placed in reservoirs 54 and 53 respectively, the analyte moves from intersection 51 along electrophoretic flowpath 52 towards reservoir 53 and through detection region 65.

Figure 5:
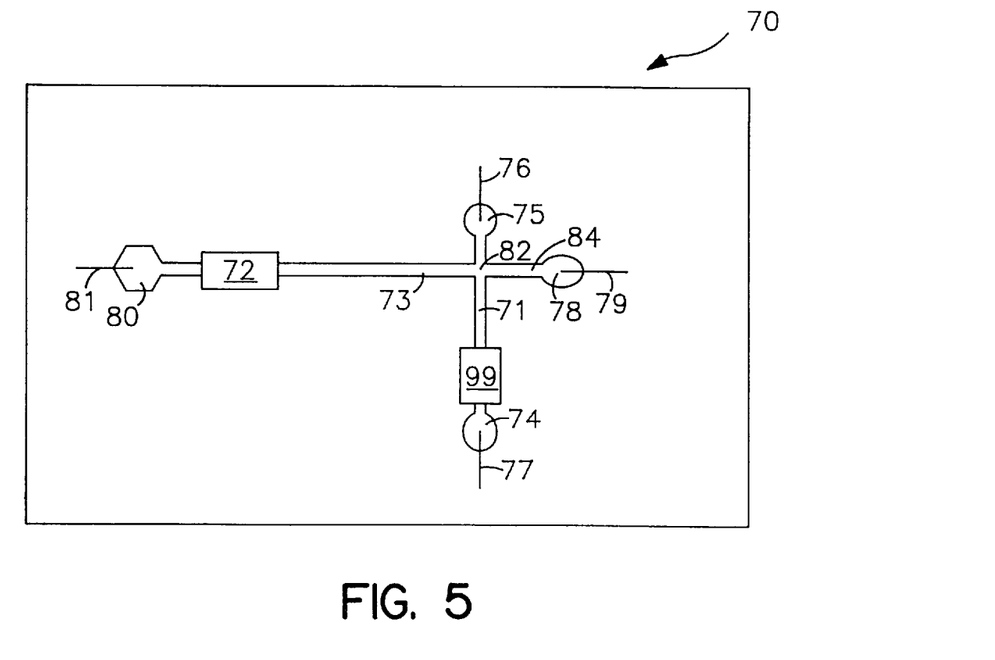
FIG. 5 provides a diagrammatic view of an embodiment of the subject invention in which the enrichment channel comprises a single fluid inlet and outlet.

FIG. 5 provides a diagrammatic top view of yet another embodiment of the subject invention in which the enrichment channel comprises a single fluid inlet and outlet. Device 70 comprises main electrophoretic flow path 71 in intersecting relationship with secondary electrophoretic flow path 73. Upstream from the intersection 82 along secondary electrophoretic flow path 73 is enrichment channel 72. In using this embodiment, sample is introduced through syringe interface 80 into enrichment channel 72, whereby the analyte comprising fraction of the sample is reversibly bound to the material present in the enrichment channel. An electric field is then applied between electrodes 81 and 79 which moves the non-reversibly bound or waste fraction of the sample out of the enrichment channel 72, along secondary electrophoretic flow path 73, past intersection 82, and out discharge outlet 84 into waste reservoir 78. An elution buffer is then introduced into enrichment channel 72 through syringe interface 80 and an electric field applied between electrodes 81 and 79, causing elution buffer to flow through enrichment channel 72 into secondary flow electrophoretic flow path 73, carrying analyte along with it. When analyte reaches intersection 82, the electric field between electrodes 79 and 81 is replaced by an electric field between electrodes 76 and 77, which causes analyte to move along main electrophoretic flow path 71 and towards reservoir 74 through detection region 99.

Figure 6:
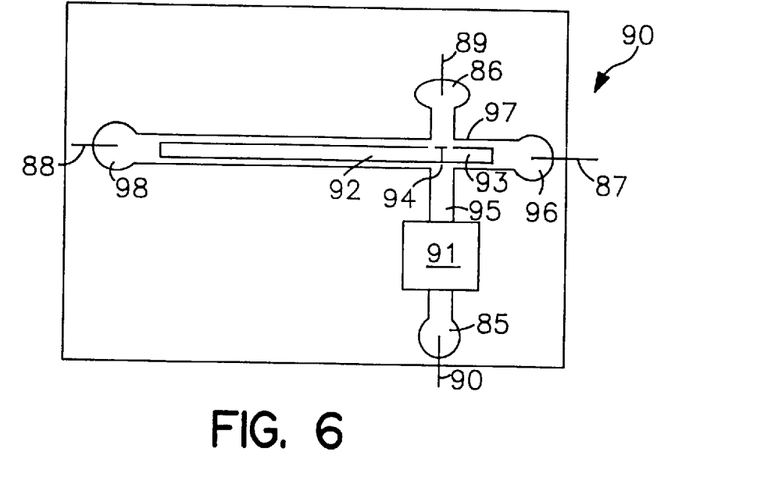
FIG. 6 provides a diagrammatic view of a device according to the subject invention in which the enrichment channel comprises an electrophoretic gel medium instead of the chromatographic material, as shown in FIGS. 1 and 2.

The device shown diagrammatically in FIG. 6 comprises an enrichment channel having an electrophoretic enrichment means, instead of the chromatographic enrichment means of the devices of FIGS. 1 to 5. In device 90, sample is introduced into reservoir 96 and an electric field is applied between electrodes 87 and 88, causing the sample to migrate towards reservoir 98. As the sample migrates towards reservoir 98 it enters stacking gel 93 having a relatively large pore size and travels towards secondary gel 92 of relatively fine pore size. At interface 94, the sample components are compressed into a narrow band. At this point, the electric field between electrodes 87 and 88 is replaced by an electric field between electrodes 89 and 90, which causes the narrow band of sample components at interface 93 to migrate into main electrophoretic flowpath 95, past detection region 91 and towards reservoir 85. In device 90, instead of the stacking gel configuration, one could provide for a molecular size membrane at the region of interface 93, which can provide for selective passage of sample components below a threshold mass and retention at the membrane surface of components in excess of the threshold mass. In yet another modification of the device shown in FIG. 6, present at the location of interface 93 could be an electrode by which an appropriate electric potential could be applied to maintain a sample component of interest in the region of 93, thereby providing for component concentration in the region of 93. For example, for an anionic analyte of interest, upon introduction of sample into reservoir 96 and application of an electric field between 93 and 87, in which 93 is the positive electrode and 87 the ground, the anionic will migrate towards and concentrate in the region of 93. After the analyte has concentrated in the region of electrode 93, an electric field can then be applied between 89 and 90 causing the anionic analyte to migrate towards reservoir 85.

Figure 7:
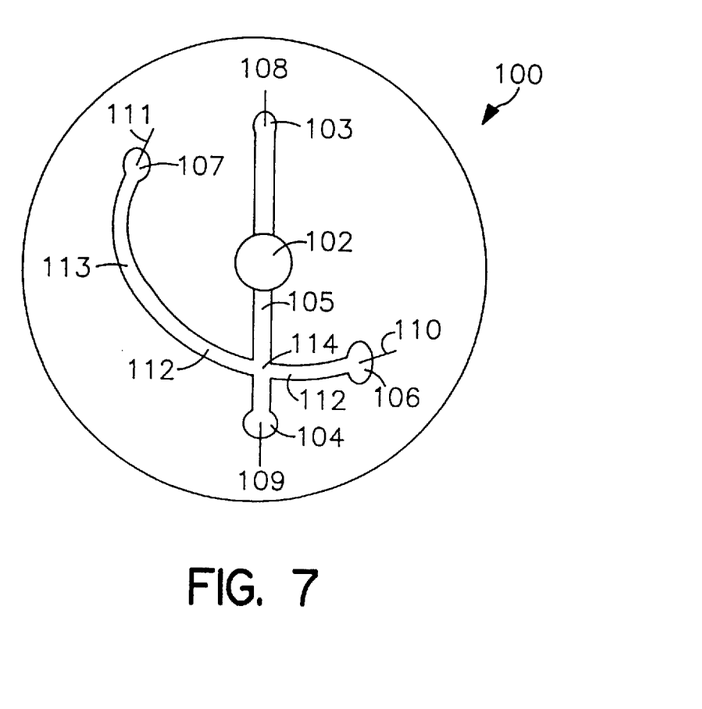
FIG. 7 provides a diagrammatic top view of disk shaped device according to the subject invention.

FIG. 7 provides a top diagrammatic view of a disk shaped embodiment of the subject device, as opposed to the credit card shaped embodiments of FIGS. 3 to 6. In device 100, sample is first introduced into enrichment channel 102. An electric field is then applied between electrodes 108 and 109, moving elution buffer 103 through enrichment channel 102, whereby analyte retained in the enrichment channel 102 is released and carried with the elution buffer to intersection 114. The electric field between 108 and 109 is then replaced with an electric field between 110 and 111, causing analyte to move from intersection 114 along main electrophoretic flow path 112, past detection region 113 and towards reservoir 107.

The subject devices may be used in a variety of electrophoretic applications, where one or more electric fields are applied to a medium to move entities through the medium. Representative electrophoretic applications include separation applications, preparation applications, sequencing applications, synthesis applications, analyte identification applications, including clinical, environmental, quality control applications, and the like. Thus, depending on the particular application a variety of different fluid samples may be introduced into the subject device, where representative samples include bodily fluids, environmental fluid samples, e.g. water and the like, or other fluid samples in which the identification and/or isolation of a particular analyte is desired. Depending on the particular application, a variety of different analytes may be of interest, including drugs, toxins, naturally occurring compounds such as peptides and nucleic acids, proteins, glycoproteins, organic and inorganic ions, steroids, and the like. Of particular interest is the use of the subject devices in clinical applications, where the samples that may be analyzed include blood, urine, plasma, cerebrospinal fluid, tears, nasal or ear discharge, tissue lysate, saliva, ocular scratchings, fine needle biopsies, and the like, where the sample may or may not need to be pretreated, i.e. combined with a solvent to decrease viscosity, decrease ionic strength, or increase solubility or buffer to a specific pH, and the like, prior to introduction into the device. For clinical applications, analytes of interest include anions, cations, small organic molecules including metabolites of drugs or xenobiotics, peptides, proteins, glycoproteins, oligosaccharides, oligonucleotides, DNA, RNA, lipids, steroids, cholesterols, and the like.

The following examples are offered by way of illustration and not by way of limitation.

EXPERIMENTAL

Example 1

High Efficiency Separation of Organic Analytes in an Aqueous Sample

A card as shown in FIG. 4 is used in the separation of organic analytes in an aqueous sample as follows in conjunction with a device that provides for the application of appropriate electric fields through introduction of electrodes into each reservoir of the card and provides for a means of detecting analyte as it passes through detection region 65. In Card 50, the enrichment channel 62 comprises porous beads coated with a C-18 phase, while the reservoirs and channels, except for the waste reservoir, comprise 20 millimolar borate buffer. A 100 $\mu$l aqueous sample is injected into enrichment channel 62 through interface 66. Substantially all of the organic analyte in the sample reversibly binds to the C18 coated porous beads, while the remaining sample components flow out of enrichment channel 62 into waste reservoir 63. 10 $\mu$l of an elution buffer (90% methanol/ 10% 20 millimolar borate buffer pH 8.3) are then introduced into the enrichment channel 62 through interface 66, whereby the reversibly bound organic analyte becomes free in the elution buffer. Because of the small volume of elution buffer employed, the concentration of analyte in the volume of elution buffer as compared to the analyte concentration in the original sample is increased 100 to 1000 times. The seals over reservoirs 57 and 56 are then removed and an electric field is applied between electrodes 61 and 60, causing buffer present in 57 to move towards 56, where movement of the buffer front moves the elution plug comprising the concentrated analyte to intersection 51. A voltage gradient is then applied between electrodes 58 and 59, causing the narrow band of analyte present in the volume of elution buffer to move through separation channel 52, yielding high efficiency separation of the organic analytes.

The above experiment is also performed in a modified version of the device depicted in FIG. 4. In the modified device, in addition to reservoir 57, the device comprises an elution buffer reservoir also in fluid communication with the enrichment channel 62. In this experiment, sample is introduced into enrichment channel 62, whereby the organic analytes present in the elution buffer reversibly bind to the C18 phase coated beads present in the enrichment channel. An electric field is applied between an electrode present in the elution buffer reservoir and electrode 60 for a limited period of time sufficient to cause 10 $\mu$l of elution buffer to migrate through the enrichment channel and release any reversibly bound organic analyte. After the elution buffer has moved into the enrichment channel, a voltage gradient is then applied between electrodes 61 and 60, resulting in the movement of buffer from 57 to 56, which carries the defined volume of organic analyte comprising elution buffer to intersection 51, as described above.

It is evident from the above results and discussion that convenient, integrated microchannel electrophoretic devices are disclosed which provide for significant advantages over currently available CE and MCE devices. Because the subject devices comprise microchannels as electrophoretic flowpaths, they provide for all of the benefits of CE and MCE devices, including rapid run times, the ability to use small sample volumes, high separation efficiency, and the like. Since the subject integrated devices comprise an enrichment channel, they can be employed for the analysis of complex sample matrices comprising analyte concentrations in the femtomolar to nanomolar range. However, because of the particular positional relationship of the enrichment channel and the main electrophoretic flowpath, the shortcomings of on-line configurations, such as band broadening and the like, do not occur in the subject devices. As the subject devices are integrated and compact, they are easy to handle and can be readily used with automated devices. Finally, with the appropriate selection of materials, the devices can be fabricated so as to be disposable. Because of their versatility and the sensitivity they provide, the subject devices are suitable for use in a wide variety of applications, including clinical electrophoretic assays.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A device for use in electrophoretic application, said device comprising a substrate having a generally planar surface on which are formed:
   a main electrophoretic microchannel defining a main electrophoretic flowpath, said main electrophoretic microchannel being provided with means for applying an electric field to media contained therein;
   an enrichment channel defining an enrichment flowpath in fluid conducting relation with said main electrophoretic flowpath, said enrichment channel containing an enrichment medium for enriching a particular fraction of a sample; and
   means for transferring a portion at least of said fraction from said enrichment channel to said main electrophoretic flowpath;
   said device further comprising an outlet in fluid conducting relation to said enrichment flowpath for discharging away from said main electrophoretic flowpath a portion of said sample other than said portion of said fraction.

2. The device according to claim 1 wherein said means for applying an electric field comprises at least one pair of electrodes connected to a source of electrical power for applying an electric field to said medium contained within said flowpath.

3. The device according to claim 1 wherein said enrichment channel further comprises an enriched fraction fluid outlet and is in direct fluid communication with said main electrophoretic flowpath, wherein said means for transferring said portion of said fraction is said enriched fraction fluid outlet.

4. The device according to claim 1 wherein said means for transferring said fraction comprises a secondary microchannel in fluid conducting relation with said enrichment flowpath and with said main electrophoretic flowpath said secondary microchannel defining a secondary flowpath.

5. The device according to claim 1, said device further comprising a waste reservoir in fluid communication with said outlet.

6. The device according to claim 1 wherein said enrichment medium comprises a chromatographic material.

7. The device according to claim 1 wherein said enrichment medium comprises an electrophoretic gel medium.

8. A device for use in electrophoretic application, said device comprising a substrate having a generally planar surface on which are formed:
   a main electrophoretic microchannel of capillary dimension defining a main electrophoretic flowpath, said main electrophoretic microchannel being provided with means for applying an electrical field to media contained therein and reservoirs at either end for introducing fluid into said flowpath;
   an enrichment channel defining an enrichment flowpath in fluid conducting relation with said main electrophoretic flowpath, said enrichment channel containing a chromatographic medium for enriching a particular fraction of a sample; and
   a secondary electrophoretic microchannel defining a secondary electrophoretic flowpath in fluid conducting relation with said enrichment flowpath and said main electrophoretic flowpath for transferring a portion at least of said fraction from said enrichment channel to said main electrophoretic microchannel; and
   at least one pair of electrodes associated with each of said main and secondary electrophoretic microchannels;
   said device further comprising an outlet in fluid conducting relation to said enrichment flowpath for discharging away from said main electrophoretic flowpath a portion of said sample other than said portion at least of said fraction.

9. The device according to claim 8, said enrichment channel further comprising means for controlling fluid flow within said enrichment channel.

10. The device according to claim 8 wherein said outlet is in fluid communication with a waste reservoir.

11. The device according to claim 8 wherein outlet is the only fluid outlet of said enrichment channel.

12. The device according to claim 8, said enrichment channel further comprising an enriched fraction fluid outlet in fluid conducting relation with said secondary electrophoretic flowpath.

13. A device for use in electrophoretic application, said device comprising a substrate having a generally planar surface on which are formed:

a main electrophoretic microchannel defining a main electrophoretic flowpath of capillary dimension said main electrophoretic flowpath containing a first medium, said main electrophoretic microchannel comprising means for introducing fluid into said flowpath and at least one pair of electrodes connected to a source of electric power for applying an electric field to said medium;

an enrichment channel comprising a sample inlet, a waste fluid outlet, and an enriched fraction fluid outlet in fluid communication with said main electrophoretic flowpath, said enrichment channel containing a chromatographic medium different from said first medium for enriching a particular fraction of a sample; and a discharge outlet in fluid conducting relation to said waste fluid outlet for discharging a portion of said sample other than said fraction away from said main electrophoretic flowpath.

14. The device according to claim 13 wherein said discharge outlet is in fluid communication with a waste reservoir.

\* \* \* \* \*